United States Patent
Fukumoto et al.

(10) Patent No.: US 7,456,129 B2
(45) Date of Patent: Nov. 25, 2008

(54) SUPPORT FOR GAS-PHASE OXIDATION CATALYST AND PROCESS FOR ITS PRODUCTION, GAS-PHASE OXIDATION CATALYST, AND PROCESS FOR PRODUCING ACRYLIC ACID

(75) Inventors: Naohiro Fukumoto, Aioi (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 81 days.

(21) Appl. No.: 11/405,588

(22) Filed: Apr. 18, 2006

(65) Prior Publication Data

US 2006/0234861 A1    Oct. 19, 2006

(30) Foreign Application Priority Data

Apr. 18, 2005    (JP)    ............................. 2005-120243

(51) Int. Cl.
   *B01J 23/00*    (2006.01)
   *B01J 21/00*    (2006.01)
   *B01J 20/00*    (2006.01)

(52) U.S. Cl. .................. 502/248; 502/255; 502/312; 502/321; 502/322; 502/349; 502/350; 502/353; 502/354; 502/407; 502/415; 502/439; 502/351; 502/355

(58) Field of Classification Search .................. 502/248, 502/255, 312, 321, 322, 349, 350, 351, 353, 502/354, 355, 407, 415, 439
See application file for complete search history.

(56) References Cited

U.S. PATENT DOCUMENTS

| | | | | |
|---|---|---|---|---|
| 4,113,769 A | * | 9/1978 | Padovan et al. | ............. 562/534 |
| 4,146,732 A | * | 3/1979 | Padovan et al. | ............. 562/534 |
| 4,382,880 A | * | 5/1983 | Derrien | ....................... 502/313 |
| 4,390,736 A | * | 6/1983 | Inoue et al. | .................. 568/801 |
| 4,440,872 A | * | 4/1984 | Grenoble et al. | ............ 502/242 |
| 4,568,778 A | | 2/1986 | Imanari et al. | |
| 4,906,791 A | | 3/1990 | Imanari et al. | |
| 5,739,392 A | * | 4/1998 | Tanimoto et al. | ............ 562/535 |
| 6,326,328 B1 | * | 12/2001 | Matsuzawa | .................. 502/217 |
| 6,420,305 B1 | * | 7/2002 | Matsuzawa et al. | ......... 502/222 |
| 2003/0060659 A1 | | 3/2003 | Yunoki | |
| 2003/0125580 A1 | | 7/2003 | Yunoki | |
| 2005/0176995 A1 | | 8/2005 | Yunoki et al. | |

FOREIGN PATENT DOCUMENTS

| | | |
|---|---|---|
| EP | 0 135 145 | 3/1985 |
| EP | 0 360 874 | 4/1990 |
| EP | 1 164 120 | 12/2001 |
| EP | 1 295 636 | 3/2003 |
| EP | 1 571 137 | 9/2005 |
| JP | 8-47641 | 2/1996 |
| JP | 2002-198024 | 7/2002 |

OTHER PUBLICATIONS

Patent Abstracts of Japan, vol. 017, No. 001 (C-1014), Jan. 5, 1993 & JP 04 238806 A (Mizusawa Ind. Chem. Ltd.), Aug. 26, 1992.
Patent Abstracts of Japan, vol. 1996, No. 06, Jun. 28, 1996 & JP 08 047643 A (Nippon Shokubai Co., Ltd.), Feb. 20, 1996.
Patent Abstracts of Japan, vol. 1996, No. 06, Jun. 28, 1996 & JP 08 047441 A (Fuji Electric Co., Ltd.), Feb. 20, 1996.

* cited by examiner

*Primary Examiner*—Cam N. Nguyen
(74) *Attorney, Agent, or Firm*—Wenderoth, Lind & Ponack, LLP

(57) ABSTRACT

A support for a gas-phase oxidation catalyst, the support including a solid acid, of which acid strength ($H_0$) meets an inequality: $-5.6 \leq H_0 \leq 1.5$; a gas-phase oxidation catalyst including the above support and a complex oxide containing molybdenum and vanadium as essential components, the complex oxide being supported on the support; a process for producing acrylic acid by gas-phase catalytic oxidation of acrolein with molecular oxygen, the process including carrying out the gas-phase catalytic oxidation in a presence of the above gas-phase oxidation catalyst; and a process for producing the above support, the process including controlling an acid strength ($H_0$) of a solid acid so as to meet an inequality: $-5.6 \leq H_0 \leq 1.5$ by adjusting a calcination temperature in a preparation of the solid acid contained in the support.

7 Claims, No Drawings

SUPPORT FOR GAS-PHASE OXIDATION CATALYST AND PROCESS FOR ITS PRODUCTION, GAS-PHASE OXIDATION CATALYST, AND PROCESS FOR PRODUCING ACRYLIC ACID

BACKGROUNDS OF THE INVENTION

1. Field of the Invention

The present invention relates to a support for a gas-phase oxidation catalyst and a process for its production, a gas-phase oxidation catalyst, and a process for producing acrylic acid.

2. Description of the Prior Art

Gas-phase catalytic oxidation is suitable for large-scale production at a lower cost. Therefore, gas-phase catalytic oxidation is now widely used for the production of variable basic chemicals from petrochemical feedstocks on an industrial scale. For example, ethylene oxide is produced by the gas-phase catalytic oxidation of ethylene, and maleic anhydride is produced by the gas-phase catalytic oxidation of benzene or n-butane. In addition, (meth)acrylic acid is produced by gas-phase catalytic oxidation starting from propane or propylene, or at least one kind of compound selected from isobutylene, tert-butanol, and methyl tert-butyl ether, and providing (meth)acrylic acid through (meth)acrolein.

For these processes of gas-phase catalytic oxidation, there is usually used a catalyst comprising an active catalytic component such as a complex oxide or heteropoly acid, which is supported on an inert support such as alumina or silica.

However, when conventional gas-phase oxidation catalysts using inactive supports are used for production on an industrial scale, the yield of a final product is insufficient, and a decrease in catalytic activity is quick, thereby making catalyst life short. Therefore, the conventional gas-phase oxidation catalysts using inactive supports do not have necessarily have sufficient satisfactory catalytic performance.

Accordingly, for example, Japanese Patent Laid-open Publication No. 8-47641 discloses a method of improving the activity and stability of a catalyst by including a solid superacid, of which acid strength ($H_0$) meets an inequality: $H_0 \leq -11.93$, in a complex oxide catalyst containing molybdenum and vanadium as essential components when acrylic acid is produced by the gas-phase catalytic oxidation of acrolein. Further, Japanese Laid-open Patent Publication No. 8-47643 discloses a method of improving the activity and stability of a catalyst by including a solid superacid, of which acid strength ($H_0$) of $H_0 \leq -11.93$ in a complex oxide catalyst containing molybdenum and phosphorus as essential components when methacrylic acid is produced by the gas-phase catalytic oxidation or gas-phase catalytic oxidative dehydrogenation of at least one compound selected from methacrolein, isobutyraldehyde, and isobutyric acid.

However, in such methods using a solid superacid, a process for preparing the solid superacid is complicated, and the solid superacid is prepared separately. Therefore, these methods become expensive, and the production cost of catalyst is inevitably increased.

SUMMARY OF THE INVENTION

Under these circumstances, it is an object of the present invention to provide a support for a gas-phase oxidation catalyst, the support being easy to handle and making easy and simple the preparation of a gas-phase oxidation catalyst, wherein catalytic performance can be improved when gas-phase catalytic oxidation is carried out using the gas-phase oxidation catalyst prepared from the support, thereby making it possible to obtain a final product in a high yield; a process for producing the support; a gas-phase oxidation catalyst; and a process for producing acrylic acid.

As a result of the present inventor's extensive studies to attain the above object, they have found that, in the production of a final product by the gas-phase catalytic oxidation of a starting material compound with molecular oxygen, the use of gas-phase oxidation catalyst using a solid acid, as a support, having a specific acid strength lower than those of solid superacids can improve catalyst performance, thereby making it possible to obtain a final product in a high yield, and that a support containing a solid acid having a specific acid strength can easily and simply be prepared by adjusting a calcination temperature. These findings have led to the completion of the present invention.

That is, the present invention provides a support for a gas-phase oxidation catalyst, the support comprising a solid acid, of which acid strength ($H_0$) meets an inequality: $-5.6 \leq H_0 \leq 1.5$.

In the support of the present invention, the above solid acid may preferably comprise a (complex) oxide containing at least one kind of element selected from aluminum, silicon, titanium, and zirconium. The term "(complex) oxide" refers to an oxide or a complex oxide.

The present invention further provides a gas-phase oxidation catalyst comprising a support and a complex oxide containing molybdenum and vanadium as essential components, the complex oxide being supported on the support.

In the gas-phase oxidation catalyst of the present invention, the above complex oxide may preferably be expressed by formula (1):

$$Mo_{12}V_aW_bCu_cA_dB_eO_x \quad (1)$$

wherein Mo is molybdenum; V is vanadium; W is tungsten; Cu is copper; A is at least one kind of element selected from cobalt, nickel, iron, chromium, lead, and bismuth; B is at least one kind of element selected from antimony, niobium, and tin; O is oxygen; a, b, c, d, e, and x mean atomic ratios of V, W, Cu, A, B, and O, respectively, and meet inequalities: $2 \leq a \leq 15$, $0 \leq b \leq 10$, $0 < c \leq 6$, $0 \leq d \leq 30$, and $0 \leq e \leq 6$, respectively; and x is a numeral value determined by oxidation states of respective elements.

The present invention further provides a process for producing acrylic acid by gas-phase catalytic oxidation of acrolein with molecular oxygen, the process comprising carrying out the gas-phase catalytic oxidation in a presence of the above gas-phase oxidation catalyst.

The present invention further provides a process for producing the above support, the process comprising controlling an acid strength ($H_0$) of a solid acid so as to meet an inequality: $-5.6 \leq H_0 \leq 1.5$ by adjusting a calcination temperature in a preparation of the above solid acid contained in the support.

The support of the present invention has a specific acid strength lower than those of solid superacids. Therefore, the support of the present invention is easy to handle and makes easy and simple the preparation of a gas-phase oxidation catalyst. When gas-phase catalytic oxidation is carried out using the gas-phase oxidation catalyst prepared from the support, it is considered that the absorption and desorption of a reactant and a product on a catalyst becomes easy because the carrier has acid points, and complete oxidation is suppressed, and therefore, it becomes possible to obtain a final product in a high yield while keeping a high conversion rate of a starting material compound. Further, a process for producing the above support according to the present invention makes it possible to easily and simply control the acid strength of a solid acid only by adjusting a calcination temperature in the preparation of the solid acid contained in the support. Thus, the support of the present invention and the process for its production, the gas-phase oxidation catalyst, and the process for producing acrylic acid according to the present invention can allow the expectation of a significant reduction in the production cost of basic chemicals, such as acrylic acid, obtained by gas-phase catalytic oxidation. In addition, the present invention is not to be limited by the contents described above.

DETAILED DESCRIPTION OF THE INVENTION

The support of the present invention is a support for a gas-phase oxidation catalyst, the support comprising a solid acid, of which acid strength ($H_0$) meets an inequality: $-5.6 \leq H_0 \leq 1.5$ (such a solid acid being hereinafter referred to simply as the "solid acid" in some cases).

The term "support" as used herein refers to a supporting material on which an active catalytic component in the gas-phase catalytic oxidation is to be supported, and the support does not necessarily need to be inactive in the gas-phase catalytic oxidation. In fact, when the support of the present invention is used for a gas-phase oxidation catalyst, it is considered that the absorption and desorption of a reactant and a product on the catalyst becomes easy because the support has acid points, and complete oxidation is suppressed, and therefore, it makes possible to obtain a final product in a high yield while keeping a high conversion rate of a starting material compound. However, a substance which substantially acts as a catalyst for gas-phase catalytic oxidation is an active catalytic component, not a solid acid having a specific acid strength. Thus, in the present invention, a solid acid having a specific acid strength is referred to as a support and is distinguished from an active catalytic component.

Further, the term "starting material compound" as used herein refers to a compound as a starting material to be subjected to gas-phase catalytic oxidation, and the term "final product" as used herein refers to an objective product finally obtained by gas-phase catalytic oxidation.

In the present invention, the acid strength ($H_0$) of the solid acid is measured by the method described below in Examples. Further, the phrase "acid strength ($H_0$) meets an inequality: $-5.6 \leq H_0 \leq 1.5$" means that the acid strength ($H_0$) of the solid acid falls within the above range, that is, the acid strength ($H_0$) of the solid acid is not lower than $-5.6$ and not higher than $1.5$. Therefore, the solid acid may be composed of one kind of solid acid having an acid strength in the above range, or may be composed of two or more kinds of solid acids having the same acid strengths ($H_0$) or different acid strengths ($H_0$), so long as these acid strengths ($H_0$) fall within the above range.

The solid acid used in the present invention is not particularly limited, so long as it has the specific acid strength. Examples of the solid acid may include (complex) oxides containing at least one kind of element selected from aluminum (Al), silicon (Si), phosphorus (P), titanium (Ti), vanadium (V), zinc (Zn), zirconium (Zr), niobium (Nb), molybdenum (Mo), and tungsten (W). Specific examples of the solid acid may include alumina, silica, titania, zirconia, silica-alumina, silica-titania, silica-vanadium oxide, silica-zinc oxide, silica-zirconia, silica-molybdenum oxide, silica-tungsten oxide, alumina-titania, alumina-vanadium oxide, alumina-zinc oxide, alumina-zirconia, alumina-molybdenum oxide, alumina-tungsten oxide, titania-zirconia, titania-tungsten oxide, zinc oxide-zirconia, zeolite, and silicon-alminophosphate. These solid acids may be used alone, or two or more kinds of these solid acids may also be used in combination. In these solid acids, (complex) oxides containing at least one kind of element selected from aluminum, silicon, titanium, and zirconium are preferred, and complex oxides containing aluminum and silicon are particularly preferred.

The solid acid may take the form of a mixture containing two or more kinds of the above (complex) oxides; the form in which the above (complex) oxide(s) is (are) supported on the different kind(s) of the above (complex) oxide(s); the form of a mixture of the above (complex) oxide(s) and any other solid(s); or the form in which the above (complex) oxide(s) is (are) supported on any other solid(s), so long as the solid acid taking each of these forms has the specific acid strength.

The solid acid may be prepared from starting materials containing the constituent elements of a (complex) oxide(s). For example, the solid acid as a complex oxide containing aluminum and silicon, which is included in the above (complex) oxides, can be prepared by, for example, forming a mixture of aluminum powder, alumina sol, and colloidal silica into a desired shape, followed by calcination. In this case, the total amount of aluminum powder and alumina sol is not smaller than 60 parts by mass and not greater than 97 parts by mass, preferably not smaller than 70 parts by mass and not greater than 95 parts by mass, and more preferably not smaller than 80 parts by mass and not greater than 90 parts by mass, relative to 100 parts by mass of the total amount of aluminum powder, alumina sol, and colloidal silica. The amount of colloidal silica to be mixed is not smaller than 3 parts by mass and not greater than 40 parts by mass, preferably not smaller than 5 parts by mass and not greater than 30 parts by mass, and more preferably not smaller than 10 parts by mass and not greater than 20 parts by mass, relative to 100 parts by mass of the total amount of aluminum powder, alumina sol, and colloidal silica. The amount of aluminum powder to be mixed is not smaller than 60 parts by mass and not greater than 97 parts by mass, preferably not smaller than 70 parts by mass and not greater than 96 parts by mass, and more preferably not smaller than 85 parts by mass and not greater than 95 parts by mass, relative to 100 parts by mass of the total amount of aluminum powder and alumina sol. The amount of alumina sol to be mixed is not smaller than 3 parts by mass and not greater than 40 parts by mass, preferably not smaller than 4 parts by mass and not greater than 30 parts by mass, and more preferably not smaller than 5 parts by mass and not greater than 15 parts by mass, relative to 100 parts by mass of the total amount of aluminum powder and alumina sol. The calcination temperature may preferably be not lower than 600° C. and not higher than 1,300° C., more preferably not lower than 650° C. and not higher than 1,200° C., and more preferably not lower than 700° C. and not higher than 1,100° C. The calcination time may preferably be not shorter than 0.5 hours and not longer than 50 hours, more preferably not shorter than 1 hour and not longer than 20 hours.

The method of controlling the acid strength of a solid acid is not particularly limited, so long as it is a method which can control the acid strength of a solid acid in such a manner that the solid acid has the specific acid strength, but a method which the present inventors have found out, that is, a method of adjusting a calcination temperature in the preparation of the solid acid, is preferred. The acid strength of a solid acid can also be controlled by using, for example, a method of changing the kind and/or ratio of constituent elements of a complex oxide.

The shape of the support is not particularly limited, so long as an active catalytic component can be supported on the support. The support may take any of conventionally well-known shapes such as powder, particle, granule, sphere, lump, pellet, fracture, fiber, needle, column, and plate. The support may have a size appropriately adjusted according to the type of usage, although it is not particularly limited to specific shapes.

The support of the present invention may preferably be used for a gas-phase oxidation catalyst in which a complex oxide containing molybdenum and vanadium as essential components is supported as an active catalytic component on the support.

In the gas-phase oxidation catalyst of the present invention, the above complex oxide as an active catalytic component may preferably be expressed by formula (1)

$$Mo_{12}V_aW_bCu_cA_dB_eO_x \quad (1)$$

wherein Mo is molybdenum; V is vanadium; W is tungsten; Cu is copper; A is at least one kind of element selected from cobalt, nickel, iron, chromium, lead, and bismuth; B is at least one kind of element selected from antimony, niobium, and tin; O is oxygen; a, b, c, d, e, and x mean the atomic ratios of V, W, Cu, A, B, and O, respectively, and meet inequalities: $2 \leq a \leq 15$, $0 \leq b \leq 10$, $0 < c \leq 6$, $0 \leq d \leq 30$, and $0 \leq e \leq 6$, respectively; and x is a numeral value determined by the oxidation states of the respective elements.

In the gas-phase oxidation catalyst of the present invention, the rate of the complex oxide supported on the support is expressed by the following equation:

Supported rate (%)=[mass of complex oxide/(mass of complex oxide+mass of support)]×100, and specifically, this rate may preferably be not lower than 5% and not higher than 70%, more preferably not lower than 10% and not higher than 60%, and still more preferably not lower than 15% and not higher than 55%.

The gas-phase oxidation catalyst of the present invention may take a shape appropriately selected according to the shape of the support, although it is not particularly limited to specific shapes.

In the present invention, the gas-phase oxidation catalyst in which a complex oxide containing molybdenum and vanadium as essential components is supported on the support can be prepared by any of the methods usually used for preparing this kind of catalyst. The starting material to be used for preparing the catalyst is not particularly limited. There can be used usually available ammonium salts, nitrates, carbonates, sulfates, hydroxides, and oxides of the respective metal elements. There can also be used compounds containing two or more metal elements. The method of allowing a complex oxide containing molybdenum and vanadium as essential components to be supported on the support is not particularly limited, but may be any of the methods usually used. For example, the gas-phase oxidation catalyst of the present invention can be obtained by allowing an aqueous solution, a suspension, or a powder, each containing a starting material, to be supported on the previously prepared support through impregnation, spraying, or evaporation to dryness, followed by drying, if necessary; and subsequent calcination of the support with the starting material supported thereon at a temperature of preferably not lower than 300° C. and not higher than 600° C., more preferably not lower than 320° C. and not lower than 550° C., and still more preferably not lower than 350° C. and not higher than 500° C., for about 1 to 10 hours.

The gas-phase oxidation catalyst of the present invention may contain any of conventionally well-known reinforcing agents to be added for the purpose of improving the strength and degree of powdering of the catalyst.

The gas-phase oxidation catalyst of the present invention is suitable for the production of acrylic acid by the gas-phase catalytic oxidation of acrolein with molecular oxygen. In this case, a substance which substantially acts as a catalyst of the gas-phase catalytic oxidation is a complex oxide containing molybdenum and vanadium as essential components, preferably a complex oxide expressed by the above formula (1), not a solid acid having the specific acid strength. Thus, in the present invention, by referring to the above complex oxide as an active catalytic component and the solid acid as a support, they are distinguished from each other.

Accordingly, the process for producing acrylic acid according to the present invention is characterized in that when acrylic acid is produced by the gas-phase catalytic oxidation of acrolein with molecular oxygen, the gas-phase catalytic oxidation is carried out in the presence of the gas-phase oxidation catalyst as described above.

The process for producing acrylic acid according to the present invention can be carried out in substantially the same manner as in any of the ordinary processes for producing acrylic acid by the gas-phase catalytic oxidation of acrolein, except that the gas-phase oxidation catalyst as described above is used. Therefore, a reactor, as well as reaction conditions, to be used in the process for producing acrylic acid according to the present invention, is not particularly limited. For example, any of the ordinary reactors such as fixed bed reactors, fluid bed reactors, and moving bed reactors can be used as a reactor. In addition, as for reaction conditions, the gas-phase catalytic oxidation may be carried out by, for example, bringing a mixed gas, as a feed gas, containing: acrolein at an amount of not smaller than 1% by volume and not greater than 15% by volume, preferably not smaller than 4% by volume and not greater than 12% by volume; oxygen at an amount of not smaller than 0.5% by volume and not greater than 25% by volume, preferably not smaller than 2% by volume and not greater than 20% by volume; steam at an amount of not smaller than 1% by volume and not greater than 30% by volume, preferably not smaller than 3% by volume and not greater than 25% by volume; and an inert gas, such as nitrogen, at an amount of not smaller than 20% by volume and not greater than 80%, preferably not smaller than 50% by volume and not greater than 70% by volume, in contact with the gas-phase oxidation catalyst to effect reactionat a temperature of not lower than 200° C. and not higher than 400° C., preferably not lower than 220° C. and not higher than 380° C., under a pressure of not lower than 0.1 MPa and not higher than 1 MPa, preferably not lower than 0.1 MPa and not higher than 0.8 MPa, and at a space velocity (under STP, i.e., standard temperature and pressure) of not lower than 300 h$^{-1}$ and not higher than 5,000 h$^{-1}$, preferably not lower than 500 h$^{-1}$ and not higher than 4,000 h$^{-1}$. As a feed gas, a mixed gas containing acrolein, oxygen, and an inert gas, such as described above, and besides, a mixed gas obtained by the addition, if necessary, of air or oxygen and steam to an acrolein-containing gas obtained by the direct oxidation of propylene, can be used. In practice, unreacted propylene or by-products such as acrylic acid, acetic acid, carbon dioxide, and propane, contained in the acrolein-containing gas obtained by the direct oxidation of propylene, have no harmful effects on the gas-phase oxidation catalyst of the present invention.

The gas-phase catalytic oxidation under such conditions provides an acrylic acid-containing gas. The resulting acrylic acid-containing gas is then subjected to post-treatment such as collection, dehydration, separation, and purification, usually carried out in any of the processes for producing acrylic acid. Thus, acrylic acid is obtained as the final product.

The support of the present invention, as demonstrated below in Examples, is easy to handle and makes easy and simple the preparation of a gas-phase oxidation catalyst. When gas-phase catalytic oxidation is carried out using the gas-phase oxidation catalyst prepared from the support, it becomes possible to obtain a final product in a high yield while keeping a high conversion rate of a starting material compound.

EXAMPLES

The present invention will hereinafter be described more specifically by reference to Examples and Comparative Examples, but the present invention is not limited to these Examples. The present invention can be put into practice after appropriate modifications or variations within a range meeting the gists described above and below, all of which are included in the technical scope of the present invention.

In the following Examples 1 to 2 and Comparative Examples 1 to 2, some experiments of producing acrylic acid by the gas-phase catalytic oxidation of acrolein with molecular oxygen were carried out. At this time, catalyst performance was evaluated by carrying out the gas-phase catalytic oxidation with catalysts in which various solid acids having different acid strengths ($H_0$) are used as supports.

<Measurement of Acid Strength>

The acid strength ($H_0$) of a solid acid is determined as follows. When a sample to be measured is white colored, the sample is immersed in benzene, to which a benzene solution containing an acid-base indicator having a known pKa value is added, and a color change, to acidic color, of the indicator on the surface of the sample is observed. It is assumed that the acid strength ($H_0$) of the solid acid is between the greatest pKa value of the pKa values of the indicators which do not change color to the acidic color and the smallest pKa value of the pKa values of the indicators which change color to the acidic color. Further, when all of the indicators used change color to the acidic color, it is assumed that the acid strength ($H_0$) is lower than the smallest pKa value of the pKa values of the indicators, and when all of the indicators used do not change color to the acidic color, it is assumed that the acid strength ($H_0$) is higher than the greatest pKa value of the pKa values of the indicators. Indicators used for the measurement of an acid strength are as follows. Indicator name (pKa value): benzalacetophenone (−5.6), dicinnamalacetone (−3.0), and 4-benzeneazodiphenylamine (1.5).

When a sample to be measured is not white colored, first, the sample is placed in a vessel having a gas discharging line and a gas introduction line, and air is sufficiently discharged from the vessel. Then, an ammonia gas is introduced into the vessel, and the ammonia is adsorbed on the sample. Then, a sample temperature is increased while discharging this ammonia gas, and the ammonia gas discharged at each temperature is collected by liquid nitrogen and the amount of the collected ammonia per mass of the sample is measured. The acid strength ($H_0$) of the sample is determined from the obtained measurement value based on a calibration curve which has separately been prepared using solid acids having known acid strengths ($H_0$).

<Evaluation of Catalyst Performance>

The catalyst performance was evaluated by the conversion rate of acrolein and the yield of acrylic acid, both of which are defined by the following equations:

Conversion rate of acrolein (%)=(mole number of reacted acrolein/mole number of fed acrolein)×100

Yield of acrylic acid (%)=(mole number of produced acrylic acid/mole number of fed acrolein)×100

Example 1

First, 75 parts by mass of γ-aluminum powder having an average particle diameter of 2 to 10 μm and 5 parts by mass of methyl cellulose as an organic binder were put into a kneader, followed by well mixing. Then, to this mixture were added 8 parts by mass (as an $Al_2O_3$ content) of alumina sol having an average particle diameter of 2 to 20 nm and 17 parts by mass (as a $SiO_2$ content) of colloidal silica having an average particle diameter of 2 to 20 nm, into which water was further put, and the mixture was well mixed to give an alumina mixture containing silica added. Then, this mixture was molded by extraction, followed by drying and calcination at 1,000° C. for 2 hours, to give a solid acid which was composed of a complex oxide in the form of particles having an average particle diameter of 7.5 mm. The acid strength ($H_0$) of the solid acid obtained met an inequality: $-3.0 \leq H_0 \leq 1.5$.

To 2 liters of water were added 350 g of ammonium paramolybdate, 96.6 g of ammonium metavanadate, 44.6 g of ammonium paratungstate, and 12.5 g of ammonium dichromate while heating and stirring the water, followed by well mixing, to give an aqueous solution. Separately, 87.8 g of cupric nitrate and 4.8 g of antimony trioxide were added to 0.2 liters of water while heating and stirring the water. Both solutions were mixed, and the resulting mixed suspension was put into a ceramics evaporator on a water bath, to which 1.2 liters of the above solid acid was added as a support, and the mixture was evaporated to dryness while stirring, followed by calcination at 400° C. for 6 hours, to give a gas-phase oxidation catalyst in which a complex oxide containing molybdenum and vanadium as essential components was supported on the support containing the solid acid, of which acid strength ($H_0$) met an inequality: $-3.0 \leq H_0 \leq 1.5$. The composition, excluding oxygen, of this catalyst, other than the support, was $Mo_{12}V_{4.6}Cu_{2.2}Cr_{0.6}W_{2.4}Sb_{0.2}$ in terms of atomic ratios. In addition, the supported rate of the catalyst was 23%.

One liter of the gas-phase oxidation catalyst was filled into a stainless reaction tube of 25 mm in inner diameter, and a mixed gas containing 5% by volume of acrolein, 5.5% by volume of oxygen, 25% by volume of steam, and 64.5% by volume of nitrogen was introduced into the reaction tube through a gas inlet of the reaction tube at a space velocity of 1,500 $h^{-1}$ (STP) to effect a gas-phase catalytic oxidation. At this time, the reaction temperature was 260° C.

As for the catalyst performance, the conversion rate of acrolein was 98.9%, and the yield of acrylic acid was 95.1%.

Example 2

A gas-phase oxidation catalyst was prepared in the same manner as described in Example 1, except that the calcination temperature of a solid acid was changed from 1,000° C. to 700° C. to give a solid acid, and the gas-phase catalytic oxidation was carried out under the same conditions as those used in Example 1. The results are shown in Table 1. Further, the acid strength ($H_0$) of the solid acid met an inequality: $-5.6 \leq H_0 \leq -3.0$.

Comparative Example 1

A gas-phase oxidation catalyst was prepared in the same manner as described in Example 1, except that the calcination temperature of a solid acid was changed from 1,000° C. to 1,400° C. to give a solid acid, and the gas-phase catalytic oxidation was carried out under the same conditions as those used in Example 1. The results are shown in Table 1. Further, the acid strength ($H_0$) of the solid acid met an inequality: $H_0 > 1.5$.

Comparative Example 2

A gas-phase oxidation catalyst was prepared in the same manner as described in Example 1, except that the calcination temperature of a solid acid was changed from 1,000° C. to 500° C. to give a solid acid, and the gas-phase catalytic oxidation was carried out under the same conditions as those used in Example 1. The results are shown in Table 1. Further, the acid strength ($H_0$) of the solid acid met an inequality: $H_0 < -5.6$.

TABLE 1

| | Acid strength of support $H_0$ | Calcination temperature of support (° C.) | Conversion rate of acrolein (%) | Yield of acrylic acid (%) |
|---|---|---|---|---|
| Example 1 | $-3.0 \leq H_0 \leq 1.5$ | 1,000 | 98.9 | 95.1 |
| Example 2 | $-5.6 \leq H_0 \leq -3.0$ | 700 | 98.7 | 94.4 |
| Comp. Ex. 1 | $H_0 > 1.5$ | 1,400 | 98.4 | 90.3 |
| Comp. Ex. 2 | $H_0 < -5.6$ | 500 | 99.0 | 88.2 |

As can be seen from Table 1, both Example 1 in which the solid acid, of which acid strength ($H_0$) met an inequality: $-3.0 \leq H_0 \leq 1.5$, was used as a support, and Example 2 in which the solid acid, of which acid strength ($H_0$) met an inequality: $-5.6 \leq H_0 \leq -3.0$ was used as a support, exhibited high conversion rates of acrolein and high yields of acrylic acid. In contrast, both Comparative Example 1 in which the solid acid, of which acid strength ($H_0$) met an inequality: $H_0 > 1.5$, was used as a support, and Comparative Example 2 in which the solid acid, of which acid strength ($H_0$) met an inequality: $H_0 < -5.6$ was used as a support, exhibited a relatively low yield of acrylic acid. From these facts, it is found that when the solid acid, of which acid strength ($H_0$) meets an inequality: $-5.6 \leq H_0 \leq 1.5$, is used as a support, acrylic acid can be produced in a high yield while keeping a high conversion rate of acrolein.

The support of the present invention is easy to handle and makes easy and simple the preparation of a gas-phase oxidation catalyst. When gas-phase catalytic oxidation is carried out using the gas-phase oxidation catalyst prepared from the support, catalyst performance is improved, and as a result, it becomes possible to obtain a final product in a high yield. Further, the process for producing the support according to the present invention makes it possible to easily and simply control the acid strength of a solid acid contained in the support. Thus, the support and the process for its production, the gas-phase oxidation catalyst, and the process for producing acrylic acid according to the present invention can significantly reduce the production cost of basic chemicals, such as acrylic acid, obtained by gas-phase catalytic oxidation, and therefore, they make a great contribution to the production fields and application fields of these basic chemicals.

The invention claimed is:

1. A gas-phase oxidation catalyst comprising a support comprising a solid acid, of which acid strength ($H_0$) meets an inequality: $-5.6 \leq H_0 \leq 1.5$, and
    a complex oxide containing molybdenum and vanadium as essential components, the complex oxide being supported on the support.

2. The gas-phase oxidation catalyst according to claim 1, wherein the complex oxide is expressed by formula (1):

$$Mo_{12}V_aW_bCu_cA_dB_eO_x \quad (1)$$

wherein Mo is molybdenum; V is vanadium; W is tungsten; Cu is copper; A is at least one element selected from the group consisting of cobalt, nickel, iron, chromium, lead, and bismuth; B is at least one element selected from the group consisting of antimony, niobium, and tin; O is oxygen; a, b, c, d, e, and x mean atomic ratios of V, W, Cu, A, B, and O, respectively, and meet inequalities: $2 \leq a \leq 15$, $0 \leq b \leq 10$, $0 < c \leq 6$, $0 \leq d \leq 30$, and $0 \leq e \leq 6$, respectively; and x is a numeral value determined by oxidation states of respective elements.

3. The gas-phase oxidation catalyst according to claim 1, wherein the solid acid comprises a (complex) oxide containing at least one element selected from the group consisting of aluminum, silicon, titanium, and zirconium.

4. The gas-phase oxidation catalyst according to claim 1, wherein the rate of the complex oxide supported on the support is not lower than 5% and not higher than 70%.

5. The gas-phase oxidation catalyst according to claim 1, wherein the rate of the complex oxide supported on the support is not lower than 10% and not higher than 60%.

6. The gas-phase oxidation catalyst according to claim 1, wherein the rate of the complex oxide supported on the support is not lower than 15% and not higher than 55%.

7. A process for producing acrylic acid by gas-phase catalytic oxidation of acrolein with molecular oxygen, the process comprising carrying out the gas-phase catalytic oxidation in a presence of a gas-phase oxidation catalyst as set forth in claim 1.

\* \* \* \* \*